United States Patent
Hartl et al.

(10) Patent No.: US 10,383,195 B2
(45) Date of Patent: Aug. 13, 2019

(54) SURGICAL LIGHT AND METHOD FOR OPERATING A SURGICAL LIGHT

(71) Applicant: TRUMPF MEDIZIN SYSTEME GMBH + CO. KG, Saalfeld (DE)

(72) Inventors: Johannes Hartl, Moosburg (DE); Deniz Güvenc, Munich (DE); Michael Schmid, Grobenzell (DE); Ingo Doser, Titisee-Neustadt (DE)

(73) Assignee: TRUMPF MEDIZIN SYSTEME GMBH + CO. KG, Saalfeld (DE)

( * ) Notice: Subject to any disclaimer, the term of this patent is extended or adjusted under 35 U.S.C. 154(b) by 130 days.

(21) Appl. No.: 15/524,836

(22) PCT Filed: Nov. 3, 2015

(86) PCT No.: PCT/EP2015/075647
§ 371 (c)(1),
(2) Date: May 5, 2017

(87) PCT Pub. No.: WO2016/071371
PCT Pub. Date: May 12, 2016

(65) Prior Publication Data
US 2017/0318644 A1    Nov. 2, 2017

(30) Foreign Application Priority Data
Nov. 7, 2014 (DE) .......................... 10 2014 222 794

(51) Int. Cl.
*H05B 37/02* (2006.01)
*A61B 90/30* (2016.01)
(Continued)

(52) U.S. Cl.
CPC ......... *H05B 37/0227* (2013.01); *A61B 90/30* (2016.02); *A61B 2017/00017* (2013.01);
(Continued)

(58) Field of Classification Search
CPC .............. A61B 2090/309; A61B 90/30; F21W 2131/205; H05B 37/0227
See application file for complete search history.

(56) References Cited

U.S. PATENT DOCUMENTS 6,880,975 B2    4/2005   Ishihara
2003/0185009 A1  10/2003  Walters
(Continued)

FOREIGN PATENT DOCUMENTS

CN   101858537       10/2010
DE   60300647 T2     2/2006
(Continued)

OTHER PUBLICATIONS

PCT Search Report and Written Opinion for PCT/EP2015/075647, completed Jan. 29, 2016.
(Continued)

*Primary Examiner* — Douglas W Owens
*Assistant Examiner* — Pedro C Fernandez
(74) *Attorney, Agent, or Firm* — Barnes & Thornburg LLP

(57) ABSTRACT

A surgical lamp for illuminating a surgical field on a human body is provided. The surgical lamp comprises a control device (4), a lamp body (1) comprising several illuminants (3) with one respective light ray (I, II, II') directed to the surgical field, and a 3D sensor (6) for detecting a spatial position of at least one object, and a device for switching on and off and dimming the illuminants (3), wherein the control device (4) controls the devices for switching on and off and dimming the illuminants (3), the 3D sensor (6) detects the spatial positon of the at least one object and transmits corresponding data to the control device (4), and the control device (4) is configured to control the illuminants (3) according to the spatial position of the at least one object.

25 Claims, 2 Drawing Sheets

(51) Int. Cl.
*F21W 131/205* (2006.01)
*A61B 17/00* (2006.01)

(52) U.S. Cl.
CPC .............. *A61B 2017/00207* (2013.01); *A61B 2090/309* (2016.02); *F21W 2131/205* (2013.01)

(56) References Cited

U.S. PATENT DOCUMENTS

| | | | |
|---|---|---|---|
| 2004/0129860 A1 | 7/2004 | Thibaud | |
| 2009/0318771 A1* | 12/2009 | Marka | A61B 90/35 600/249 |
| 2011/0037840 A1* | 2/2011 | Hiltl | A61B 90/35 348/61 |
| 2012/0075832 A1* | 3/2012 | Schmid | F21V 21/403 362/33 |

FOREIGN PATENT DOCUMENTS

| | | |
|---|---|---|
| EP | 2136126 | 12/2009 |
| EP | 2283790 | 2/2011 |
| EP | 2434202 | 3/2012 |

OTHER PUBLICATIONS

English Translation of the International Preliminary Report on Patentability dated May 18, 2017.

\* cited by examiner

SURGICAL LIGHT AND METHOD FOR OPERATING A SURGICAL LIGHT

CROSS REFERENCES TO RELATED APPLICATIONS

This application is a U.S. national phase of PCT/EP2015/075647, filed on Nov. 3, 2015, which claims the benefit of and priority to German Patent Application Serial No. 102014222794.1, filed Nov. 7. 2014, both of which are incorporated herein by this reference in their entirety.

The invention relates to a surgical lamp and a method for operating a surgical lamp, in particular, a surgical lamp having automatic setting possibilities for a light field, and a method for illuminating a surgical field on a human body by this surgical lamp.

Document U.S. Pat. No. 6,880,957 B2 shows a surgical lamp, whereby each light source is equipped with a sensor. The sensor recognizes an obstacle only in the beam path of the respective light source and dims this light source in order to prevent shadowing by the obstacle.

However, thereby, merely a current position of the obstacle, namely a presence within the respective beam path, is evaluated. Thus, a changing shadowing of the surgical field cannot be predetermined and an action in advance is not possible.

Thus far, pure distance measuring devices are deployed for a distance measurement between a lamp body of the surgical lamp and the surgical field and additional specific sensors are used for further sensor based application, as e.g. the setting of a focus situations and/or light field dimensions or a gesture control.

The invention is based on the object to provide a surgical lamp providing the precondition of anticipatorily preventing or reducing shadowing and providing further operation and functional possibilities in an economical manner.

The object is achieve by a surgical lamp according to claim 1 and a method according to claim 14. Further developments of the invention are subject-matters of the dependent claims.

By a provision of a 3D sensor at a lamp body of a surgical lamp, a spatial position of an object between the lamp body and a surgical field as well as a distance of the surgical field from the lamp body as the position can be detected.

The invention is elucidated by means of embodiments referring to the attached drawings.

In particular:

FIG. 1 shows a lamp body 1 of a surgical lamp. The lamp body is fixed by a suspension device (not shown) to e.g. at a room ceiling via a pivot joint 2 in a manner pivotable in all directions.

Figure 1:
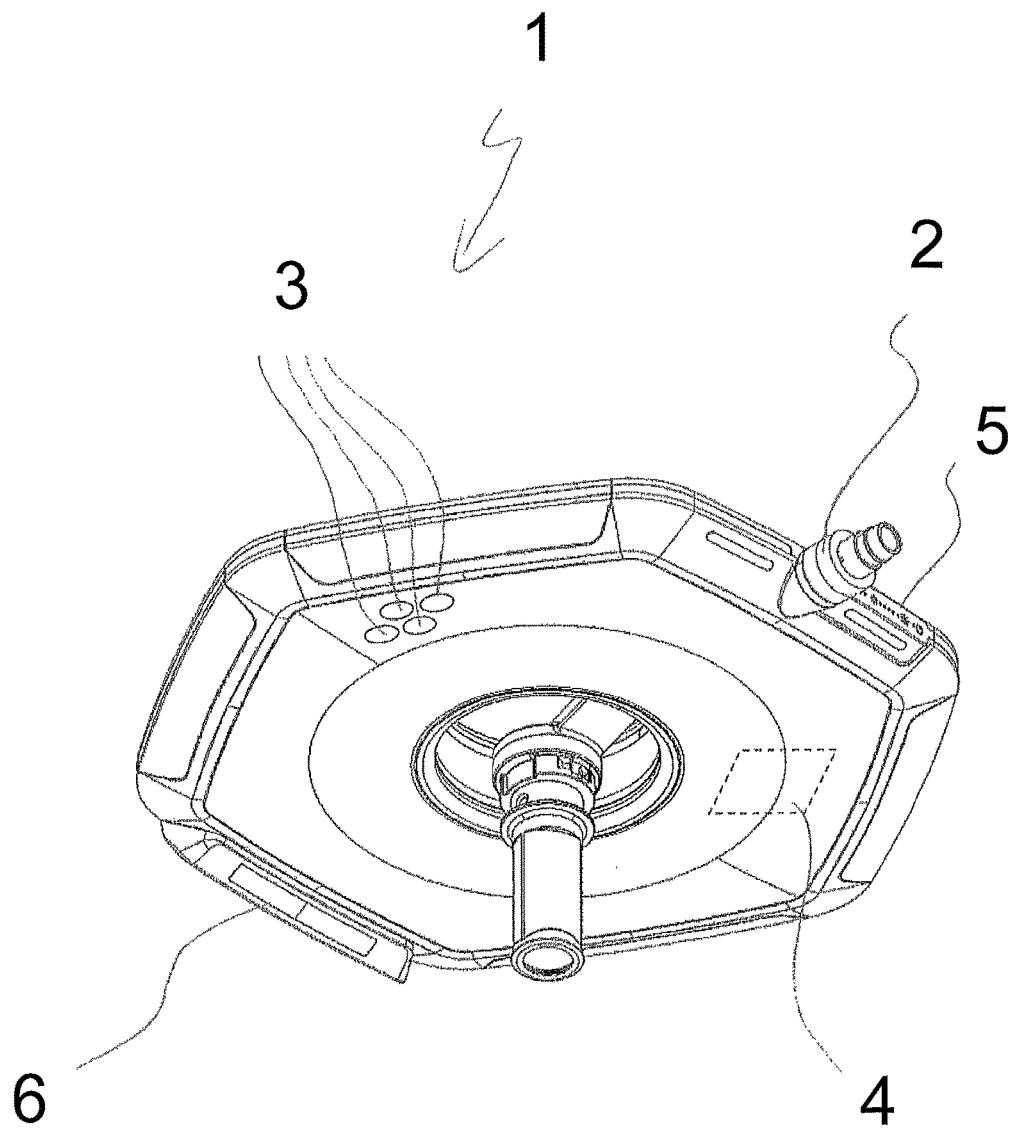
FIG. 1 shows an isometric view of a lamp boy of a surgical lamp.

The lamp body 1 is provided with several illuminants 3. The illuminants 3 are located within the lamp body 1 and, in the alignment of the lamp body 1 shown in FIG. 1, radiate light in a respective light ray downwardly. The light rays are directed to a surgical field on a human body in order to illuminate this. Only four of a plurality of the illuminants 3 are illustrated here. The illuminants 3 are carried out as LEDs here and they are basically distributed across an entire light escape area at the lamp body 1.

Further, the surgical lamp comprises a control device 4 in the lamp body 1 or, alternatively, at another suitable position, e.g. at a ceiling fixation.

Here, the surgical lamp is provided with operating elements 5 at the lamp body 1, wherein the operating elements 5 can also be provided at the suspension device or at a wall panel (not shown).

The illuminants 3 and the operating elements 5 are connected to the control device 4. The control device 4 controls the illuminants via a device (not shown) for switching on and off and dimming the illuminants according to settings at the operating elements 5. By the operating elements 5, a setting of an intensity of the light radiated by the illuminants 3, i.e. a brightness in the surgical field, and of a diameter of a light field generated by the illuminants 3 in the surgical field are possible. Optionally, further setting possibilities, e.g. a color temperature of the radiated light, are possible.

At the lamp body 1, a 3D sensor 6 for detecting a spatial position of objects, as e.g. parts of the body of the surgical personnel, surgical apparatuses or a body of a patient, or of motions of the objects is arranged. The 3D sensor 6 is connected to the control device 4 and transmits data according to the detected objects to the control device 4. The control device 4 evaluates the data of the 3D sensor 6 and controls the illuminants 3 according to the position and the motion of the objects.

Alternatively, the 3D sensor 6 can already evaluate the position of the objects and transmits accordingly processed data to the control device 4. In a further alterative, the data of the 3D sensor 6 are processed up to a defined degree by this and, then, they are finally processed by the control device 4. This is then beneficial if data, e.g. having the same format characteristic, are transferred from different sources to the control device 4. In a further alternative embodiment, the 3D sensor 6 transfers data of different processing stages if, as described later, these are differently evaluated for different functionalities. In view of functionalities of the surgical lamp based on 3D sensor data, several control devices 4 are optionally provided.

Optionally, the 3D sensor 6 additionally detects a size of the detected objects. From the data concerning the size, the spatial position and the motion of the object, the control device 4 controls the illuminants 3 such that light rays impinging on a detected object between the lamp body 1 and the surgical field are dimmed or switched off. Thereby, shadowing by the object is reduced or prevented. The illuminants 3, the light rays of which do not impinge on the object but are directed past the object to the light field, are then operated with increased performance in order to maintain an illuminance, i.e. the brightness, in the surgical field at least almost constant despite the object between the lamp body 1 and the surgical field. The larger the object is the higher is e.g. the performance with which the illuminants 3, the light rays of which do not impinge on the object, are operated. Optionally, the size of the object is also associated with its measured distance. It is assumed that the shadowing is slight upon a small distance to the lamp body 1 than upon objects with a large distance to the lamp body 1 or to the 3D sensor when focusing the light rays to the surgical field.

Thereto, a space filled by the light ray for each of the illuminants 3 is stored in a memory area of the control device 4. Under consideration of a distance information, the space can optionally be divided in further portions. When the object between the lamp body 1 and the surgical field is located at least partially in the space of the light ray or in one of the portions of the space of a certain illuminant 3, this illuminant 3 is dimmed or switched off. The amount of the dimming is determined by a proportion of a cross section of the light ray occupied by the object. The illuminants 3 adjacent to this certain illuminant 3 are then operated with increased performance.

Optionally, a contour of the detected object is also detected. In the memory area of the control device 4, different contours of the objects are stored. The illuminants 3 are then differently controlled depending on the contour of the detected object, therefore per a kind of the object. Thereby, a certain area of the surgical field can be illuminated with an increased illuminance for e.g. a certain type of surgical instrument. Upon recognizing e.g. a tissue retractor, the periphery of the surgical field is illuminated in an increased manner compared to other areas or, alternatively, a shadowing is reduced or prevented. However, when recognizing a scalpel, the center of the surgical field is illuminated in an increased manner than other areas or, alternatively, shadowing is reduced or prevented there. Therefore, the position into which the object will move and, therefore, in which manner the illuminants 3 will be controlled are predicted by the control device 4 due to the contour.

In turn as an option, the control device 4 determines a position into which the object will move, therefore, in which it will be located at a certain subsequent point of time, from a spatial position of the detected object and its motion, namely its direction and/or its velocity and/or its acceleration. Thereby, it is possible that the control device 4 prevents shadowing in real-time without a delay by a response time of the 3D sensor, the control device 4 and the illuminants 3.

Further, the control device 4 is optionally also configured to detect an object being located between the lamp body 1 and the surgical field outside of a light cone generated by the light rays, or being located within in a predetermined position. The control device 4 then determines the manner to control the illuminants 3 from a direction and/or trajectory and/or a velocity and/or an acceleration of a motion of the detected object. Thereby, it is possible to control the illuminants 3 by the control device 4, e.g. by a gesture control by means of a hand movement, in order to dim the surgical lamp or to change the light field diameter.

The light field diameter is defined such that an illuminance of 10% of an illuminance in the center of the light field exists on this diameter.

The allocation of detected objects to functions to be controlled can optionally happen via a space partition and/or specific distinctive features/characteristics. Further, by the detected objects according to the space partition, also switching between a prevention of shadowing and a gesture control can happen. Upon the space partition, different portions in direction of the light rays can be defined. For example, in the near-field of the lamp body, in particular in a region where usually the heads of the surgical personnel are located, detected objects are used for the prevention of the shadowing. In a middle region where usually the hands of the surgical personnel are located, the objects and their motions are understood as gestures for the gesture control. In a region on or directly above the surgical field, e.g. on the basis of objects or characteristics of the objects defined in advance, an alignment of the light rays can happen.

Alternatively, a region captured by the 3D sensor 6 not being illuminated can be used for the gesture control, whereas, within the spaces of the light rays, shadow prevention and alignment of the light rays, namely a position and a diameter of the light field, can be distinguished by a spatial allocation of the objects or typical characteristics. For example, almost circular objects having a certain size, implying a head, or objects comprising a marking—e.g. in a surgical head covering—are used for shadow prevention. On the other hand, for the alignment of the light rays, typical shapes of surgical tools or of surgical instruments are used.

Figure 2:
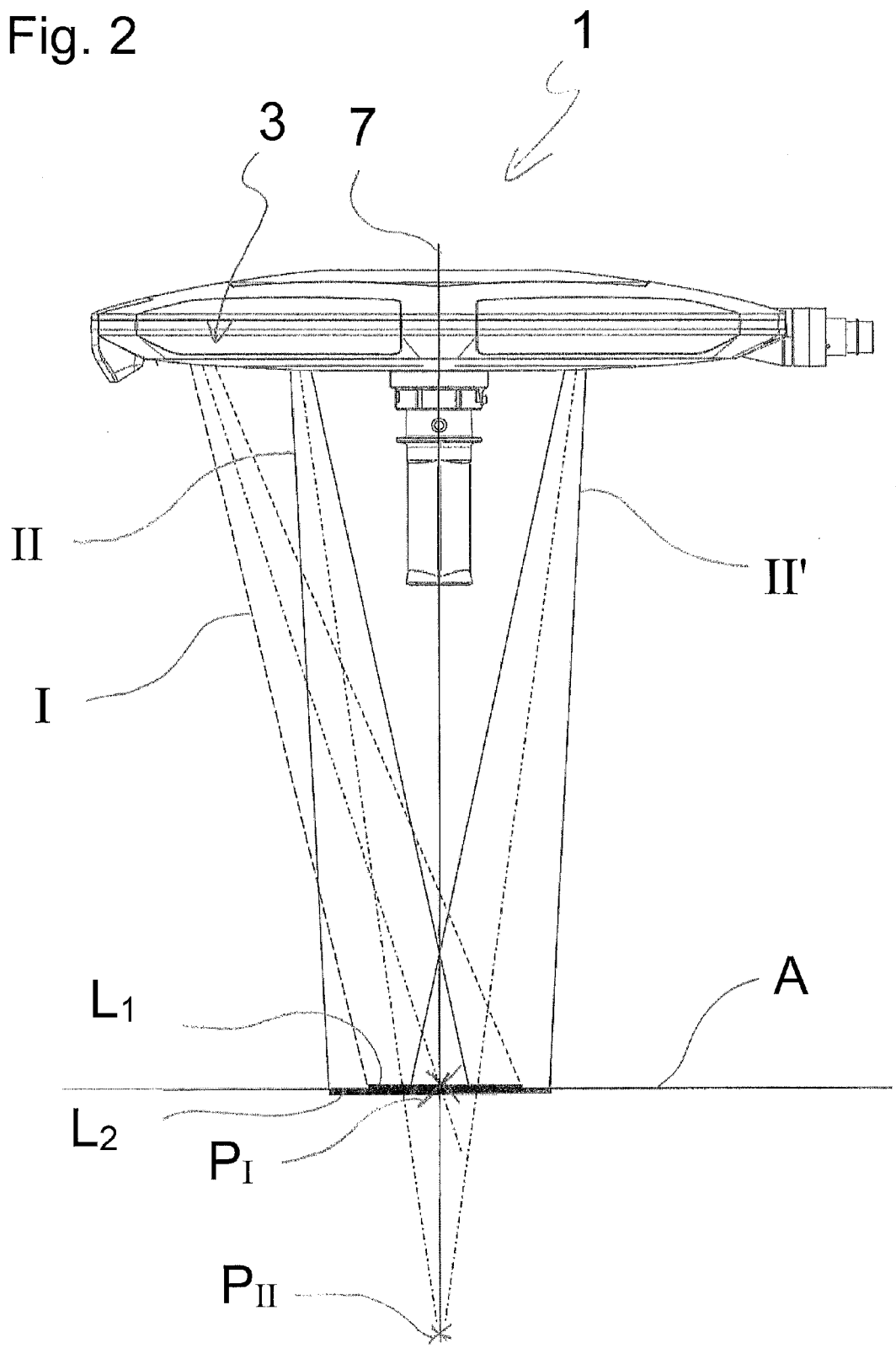
FIG. 2 shows a side view of the lamp body of FIG. 1 with exemplary light rays for generating light fields.

In FIG. 2, a side view of the lamp body 1 is shown. The lamp body 1 has a central axis 7. The illuminants 3 in the lamp body 1 radiate their light via light rays I, II, II'. Each of the illuminants 3 in the lamp body 1 emits one of the light rays I, II, II', wherein, in FIG. 2, merely the three light rays I, II, II' are illustrated for a clear illustration.

In order to explain the principle of the embodiment, the light rays I, II, II' of all of the illuminants 3 are directed to the central axis 7 of the lamp body 1, wherein, it is assumed in simplified terms that the intersection points $P_I$, $P_{II}$ are generated by each light ray I, II, II' and the central axis. As exemplarily shown by the light rays I, II, II', the light rays intersect the central axis 7 at different distances. Due to the simplified illustration including the three light rays, only two intersection points $P_I$, $P_{II}$ are shown here, wherein it is illustrated that merely the one light ray I is directed to the intersection point $P_I$ and two light rays I, II' are directed to the intersection point $P_{II}$. Actually, several intersection points of several light rays and the central axis 7 exist, wherein also several light rays (also more than two light rays as shown by means of the intersection point $P_{II}$) can intersect the central axis 7 at the same intersection point. Actually, light rays not being directed to the central axis 7 can also be provided.

The light ray I generates a light field $L_1$ and the light rays II, II' generate a light field $L_2$ on the surgical field. The light rays I, II, II' are superimposed to generate a resulting light field having a determined light field diameter and a determined light distribution in the light field. By a distinct control of the illuminants 3 by the control device 4, it is possible to adjust the light field diameter and the light distribution in the resulting light field.

In FIG. 2, a surface of the human body on which the surgical field is located is illustrated in a simplified manner by the horizontal line A. The human body which is regarded as the detected object in this context is at a spatial position which is detected as distance between the lamp body 1 and the surgical field on the surface A of the human body.

The light ray I is directed to the intersection point $P_I$ being located at the distance of the surgical field from the lamp body 1 on the central axis 7. The light rays II, II' are directed to the intersection point $P_{II}$ on the central axis not being located at the distance of the surgical field from the lamp body 1.

In order to focus the light rays I, II, II' on the surgical field, the one illuminant 3, the light rays I of which are directed to the intersection point $P_I$, the distance of which is identically equal to the distance of the surgical field from the lamp body 1, and which generates the light field $L_1$ is operated solely or with an increased performance with respect to the other illuminants 3. If no intersection point $P_I$, $P_{II}$ at the distance of the surgical field exists, those of the illuminants 3, the light rays I, II, II' of which generate an intersection point $P_1$. $P_2$, the distance of which from the lamp body 1 is closest to the distance of the surgical field from the lamp body 1, are operated. These illuminants 3 are either solely operated or together with other illuminants 3, however, then with increased performance with respect to the other illuminants 3.

Otherwise, in order to adjust a light field diameter by different controls of the illuminants 3, the control device 4 controls the illuminants 3 such that the one of the illuminants 3, the light ray I of which intersects the central axis 7 at the distance of the surgical field, as well as the ones, the light ray II, II' does not intersection the central axis 7 at the distance of the surgical field, are operated with performances geared to each other. For a light field diameter as small as possible, the ones of the illuminants 3 are operated, the light rays I of which intersect the central axis at the distance of the surgical field, in order to generate the light field $L_1$ as described above. For an enlargement of the diameter of the light field $L_1$, $L_2$, the ones of the illuminants 3, the light rays II, II' of which do not intersect the central axis 7 at the distance of the surgical field, are operated with increased performance. By these light rays II, II', the light field $L_2$, the diameter of which is larger than that of the light field $L_1$, is generated. In order to generate a light field diameter which is larger than that of the light field $L_1$ but smaller than the diameter of the light field $L_2$, the illuminants 3 generating the light field $L_1$ and the illuminants 3 generating the light field $L_2$ are respectively operated with a performance geared to each other. Thereby, when simultaneously operating the illuminants 3 generating the light field $L_1$ and the illuminants 3 generating the light field $L_2$, a light field, the resulting light field diameter of which is between the diameters of the light field $L_1$ and of the light field L2, resulting thereof can be generated. The larger the proportion of the emitted intensity of the illuminants 3 generating the determined light field diameters $L_1$ and $L_2$ of an overall performance is, the closer is the resulting light field diameter to this determined light field diameter. When the illuminants 3 are operated with a performance geared to each other, on the one hand, the resulting light field diameter is adjustable and, on the other hand, the illumination, i.e. the brightness, in the surgical field is adjustable.

By measuring the distance of the lamp body 1 from the surgical field, it is also optionally possible to control the illuminants 3 such that the illumination in the center of the surgical field remains constant upon a change of the distance. The associated power values are thereby either empirically detected and stored in the memory area of the control device 4 or calculated via an algorithm.

In a further option, a topography of the surgical field is detected. From the characteristics of the surgical field, as e.g. the size, the depth, or the inclination, the control device 4 determines which illuminants 3 are operated in order to illuminate the surgical field in a possibly optimal manner. Upon large-area surgical fields, e.g. the ones of the illuminants 3 generating a light field $L_1$, $L_2$ having a large diameter are operated. In the case of small surgical fields, the ones of the illuminants 3 generating a light field $L_1$, $L_2$ having a small diameter are operated. The diameter of the light field L1, L2 basically corresponds to the size of the surgical field. In the case of deep surgical fields, the ones of the illuminants 3, the light ray I, II, II' of which is directed possibly vertically to the surgical field are operated in order to illuminate the entire depth of the surgical field.

In a further alternative embodiment, the surgical lamp is used in a system of at least two surgical lamps.

Although each of the surgical lamps on its own complies with the admissible ranges for the illuminance in the surgical field, in a case in which the light rays are directed to the same surgical field, there is the risk that the maximum admissible illuminance is exceeded by a superposition of the light fields of several surgical lamps. Thereby, there is the risk of glare of the surgical personnel and of desiccation of the wound in the surgical field.

In order to avoid this, the spatial arrangement of the surgical field is respectively recognized by the 3D sensors 6 of the individual surgical lamps. By the respective control devices 4 of the surgical lamps, it is determined whether the light rays I, II, II' of the illuminants 3 are directed to the same surgical field and generate a light field $L_1$, $L_2$ thereon. If it is determined by the control devices 4 that the light rays I, II, II' are directed to the same surgical field, the performance of the illuminants 3 directed to the surgical field is tuned such that the maximum admissible illuminance, or optionally a settable maximum illuminance, is not exceeded.

Optionally, there is also the possibility to detect the actual illuminance in the surgical field by another kind of sensor, e.g. a brightness sensor, or to detect a temperature in the surgical field by a temperature sensor in order to avoid desiccation of the wound.

Furthermore, in the case in which several surgical lamps are directed to the same surgical field, there is the possibility to achieve shadow prevention not only by the control of the illuminants 3 of the lamp body 1, the 3D sensor of which detects the object. When detecting the object between the lamp body 1 and the surgical field, on the one hand, additionally to a dimming or switching off of the illuminants 3, the object being located in the light ray I, II, II' thereof, the other illuminants 3 of the same lamp body 1 are operated with an increased performance by the control device 4. Furthermore, the control devices 4 of the other surgical lamps being also directed to the same light field $L_1$, $L_2$, attuned with the control device 4 of the surgical lamp, the 3D sensor of which detects the object, control their illuminants 3 with an increased performance if no object is located in their respective light rays I, II, II'.

Optionally, the control device 4 of the individual surgical lamps control the illuminants 3 attuned with each other such that the illumination in the surgical filed remains at least almost constant.

In operation, a spatial position of at least one of the objects, one of the body parts of the surgical personnel or one of the surgical apparatuses, is detected by the 3D sensor 6. The corresponding data concerning the spatial position of the object are transmitted to the control device 4. Subsequently, the illuminants 3 are controlled according to the spatial position detected by the 3D sensor.

Optionally, also the size of the object being located between the lamp body 1 and the surgical field is detected. The ones of the illuminants 3, the light ray I, II, II' of which is directed to the object, are then the dimmed or switched off in order to prevent shadowing by the object. In order to compensate the reduced brightness in the surgical field caused by the switching off or the dimming, the ones of the illuminants 3, the light rays I, II, II' of which are directed past the object to the surgical field, are operated with an increased performance so that the brightness in the surgical field remains almost constant.

If, additionally to the spatial position, a motion or a contour of the object is detected, it can predicted which position will be occupied by the object at a certain point of time. Thus, e.g. from a velocity or an acceleration in a certain direction, this predetermined position at a certain point of time can be calculated. The illuminants 3 are then controlled by the control device 4 such that the illuminants 3, the respective light ray of which is directed to the predetermined position at this point of time, is not operated or only in a dimmed manner. The light rays which then are not directed to the predetermined position of the object and then are directed past the object to the surgical field are operated with increased performance as elucidated above.

The motion of the detected object is optionally not only used for shadow prevention, however, also for controlling the surgical lamp. Thus, e.g. a motion of a hand, i.e. a gesture of a surgeon, detected by the same 3D sensor 6 is used for executing a certain control of the illuminants 3 by the control device 4, e.g. a switching off or dimming, according to its direction, its trajectory, its velocity or its acceleration.

In order to focus the light rays directed to the surgical field, only or mainly the ones of the illuminants 3 which are directed to the intersection point where the light ray I of which intersects the central axis 7, or to a point which is closest to the distance of the surgical field are operated.

In order to adjust the light field diameter to a requested size, the illuminants 3 being directed to a point on the central axis 7 at the distance of the surgical field and also the illuminants 3 not being directed to the point on the central axis 7 at the distance of the surgical field are operated with the attuned performance as described above.

In order to facilitate the operation of the surgical lamp, the illuminants 3 are controlled by the control device 4 such that upon a change of the distance between the lamp body 1 and the surgical field, the illuminance in the center of the light field $L_1$, $L_2$ remains constant.

In order to illuminate the surgical field as optimally as possible, the topography of the surgical field is detected by the 3D sensor 6. From the characteristics of the surgical field, such as the size, the depth or the inclination, the control device 4 determines the illuminants 3 to be operated in order to illuminate the surgical field as described above.

The various embodiments can be combined to one another.

What is claimed is:

1. A surgical lamp for illuminating a surgical field on a human body, the surgical lamp having:
    a control device,
    a lamp body comprising
        several illuminants with one respective light ray (I, II, II') directed to the surgical field, and
        a 3D sensor for detecting a spatial position of at least one object, and devices for switching on and off and dimming the illuminants,
    wherein the control device controls the devices for switching on and off and dimming the illuminants,
    the 3D sensor detects the spatial position of the at least one object and transmits corresponding data to the control device,
    the control device is configured to control the illuminants according to the spatial position of the at least one object,
    the 3D sensor detects the spatial position and a size of the at least one object between the lamp body and the surgical field,
    the control device is configured, due to the spatial position and the size of the at least one object, to dim or to switch off the illuminants, the respective light ray (I, II, II') of which is directed to the at least one object, and to operate the illuminants, the respective light ray (I; II; II') of which is directed past the at least one object to the surgical field, and
    the control device is configured to predict an expected position of the at least one object at a certain point of time from the spatial position and the motion of the at least one object and to control the illuminants depending on the predicted positon and the size of the at least one object such that the illuminants, the respective light ray (I, II; II') of which is then directed to the at least one object in the predicted position, are dimmed or switched off at the certain point of time, and the illuminants, the respective light ray (I; II, II') of which is then directed past the at least one object in the predicted position to the surgical field.

2. The surgical lamp according to claim 1, wherein the control device is configured to determine an area of the surgical field which is to be illuminated in an increased manner from a contour of the at least one object, and the control device is operates the illuminants, the respective light beam (I, II, II') of which are directed to the area.

3. The surgical lamp according to claim 1, wherein the control device is configured to predetermine the predetermined position from a direction of the motion of the at least one object.

4. The surgical lamp according to claim 1, wherein the control device is configured to predetermine the predetermined position from a velocity of the motion of the at least one object.

5. The surgical lamp according to claim 1, wherein the control device is configured to predetermine the predetermined position from an acceleration of the motion of the at least one object.

6. The surgical lamp according to claim 1, wherein the control device is configured to control the illuminants according to a direction, a trajectory, a velocity, or an acceleration of the motion of the at least one object.

7. The surgical lamp according to claim 1,
    wherein one of the objects is the human body on which the surgical field is located,
    the spatial position corresponds to the distance of the surgical field from the lamp body,
    the lamp body comprises a central axis,
    the light rays (I, II, II') are directed to intersection points ($P_I$, $P_{II}$) with the central axis, the intersection points having different distances from the lamp body,
    the light rays (I, II, II') are superimposed in order to generate a light field ($L_1$, $L_2$) on the surgical field, and
    the control device is configured to control the illuminants such that the illuminants, the respective light ray (I, I, II') of which intersects the central axis at a distance of the surgical field or which is directed to a point, a distance of which is closest to the distance of the surgical field, are operated with a performance increased with respect to the remaining illuminants in order to focus the light rays (I, II, II') on the surgical site.

8. The surgical lamp according to claim 7, wherein
    the control device is configured to control the illuminants such that, alternatively, the ones of the illuminants, the light ray (I, II, II') of which intersects the central axis at the distance of the surgical field as well as the ones, the light ray (I, II, II') of which does not intersect the central axis at the distance of the surgical field are operated with a performance geared to each other in order to render a light field diameter adjustable.

9. The surgical lamp according to claim 7, wherein the control device is configured to control the illuminants such that an illumination in the center of the surgical field ($L_1$, $L_2$) remains constant upon a change of the distance of the surgical field.

10. The surgical lamp according to claim 1, wherein the 3D sensor is configured to detect a surface structure of the surgical field, and the control device is configured to determine a topography of the surgical field from the data transmitted by the 3D sensor, and to operate the illuminants according to the topography.

11. A method for operating a surgical lamp according to claim 1, the method comprising the following steps:
    detecting the spatial position of the at least one object by the 3D sensor and transmitting corresponding data to the control device; and controlling the illuminants according to the spatial position of the at least one object.

12. The method for operating a surgical lamp according to claim 11 with a surgical lamp comprising the additional steps:
    detecting a size of the at least one object between the lamp body and the surgical field by means of the 3D sensor;
    dimming or switching off the illuminants, the respective light ray of which is directed to the at least one object by the control device; and
    operating the illuminants, the light rays of which are directed past the at least one object to the surgical field.

13. The method according to claim 12 with a surgical lamp with the additional steps:
    predetermining a position of the at least one object at a certain point of time from the spatial position and a motion and/or a contour of the at least one object by means of the control device;
    controlling the illuminants depending on the predetermined position and the size of the at least one object so that the ones of the illuminants, the respective light ray (I, II, II') of which is directed to the at least one object at the predetermined position, are dimmed or switched off at the certain point of time, and the illuminants, the respective light ray (I, II, II') of which is directed past the at least one object at the predetermined position to the surgical field.

14. The method according to claim 13, wherein the predetermined position is predetermined from a direction, a velocity, or an acceleration of the at least one object by the control device.

15. The method according to claim 11 with the step:
    controlling the illuminants according to a direction, a trajectory, a velocity, or an acceleration of a motion of the at least one object by the control device.

16. The method according to claim 11 with the step:
    controlling the illuminants such that the illuminants, the light ray (I, II, II') of which intersects a central axis at a distance of the surgical field or is directed to a point, a distance is closest to the distance of the surgical field, are operated with a performance increased with respect to the remaining illuminants in order to focus the light rays (I, II, II') on the surgical site.

17. The method according to claim 11 with the step:
    controlling the illuminants such that the illuminants, the light ray of which intersects a central axis at a distance of the surgical field, as well as the illuminants, the light ray (I, II, II') of which does not intersect the central axis at the distance of the surgical field, are operated with a performance geared to each other by the control device in order to render adjustable a light field diameter.

18. The method according to claim 11 with the step:
    controlling the illuminants such that an illumination in a center of the surgical field remains constant upon a change of a distance of the surgical field.

19. The method according to claim 11 with the steps:
    detecting a topography from data transmitted by the 3D sensor by the control device;
    operating the illuminants by the control device such that the surgical field is illuminated according to the topography.

20. The method according to claim 19, wherein the surgical field is illuminated by the illuminants generating a light field ($L_1$, $L_2$) with a large diameter when the surgical field is widespread, and the surgical field is illuminated by the illuminants generating a light field with a small diameter when the surgical field is small so that a diameter of the light field ($L_1$, $L_2$) basically corresponds to a size of the surgical field.

21. The method according to claim 19, wherein the surgical field is illuminated by the illuminants, the light rays (I, II, II') of which are vertically directed onto the surgical field, when the surgical field includes a deep wound.

22. A system of several surgical lamps with at least one surgical lamp according to 1, wherein the control devices of several surgical lamps are configured to be controlled via data of the 3D sensor.

23. A surgical lamp for illuminating a surgical field on a human body, the surgical lamp having:
    a control device,
    a lamp body comprising
        several illuminants each with one respective light ray directed to the surgical field, and
        a 3D sensor for detecting a spatial position of at least one object, and devices for switching on and off and dimming the illuminants,
    wherein the control device controls the devices for switching on and off and dimming the illuminants,
    the 3D sensor detects the spatial position of the at least one object and transmits corresponding data to the control device, and
    the control device is configured to control the illuminants according to a predicted spatial position as determined by the movement and shape of the at least one object to prevent shadowing of the surgical field by the object.

24. A system of several surgical lamps with at least one surgical lamp according to 23, wherein the control devices of several surgical lamps are configured to be controlled via data of the 3D sensor.

25. The surgical lamp according to claim 23,
    wherein one of the objects is the human body on which the surgical field is located,
    the spatial position corresponds to the distance of the surgical field from the lamp body,
    the lamp body comprises a central axis,
    the light rays (I, II, II') are directed to intersection points ($P_I$, $P_{II}$) with the central axis, the intersection points having different distances from the lamp body,
    the light rays (I, II, II') are superimposed in order to generate a light field ($L_1$, $L_2$) on the surgical field, and
    the control device is configured to control the illuminants such that the illuminants, the respective light ray (I, I, II') of which intersects the central axis at a distance of the surgical field or which is directed to a point, a distance of which is closest to the distance of the surgical field, are operated with a performance increased with respect to the remaining illuminants in order to focus the light rays (I, II, II') on the surgical site.

* * * * *